US009101757B2

(12) United States Patent
Frenzel et al.

(10) Patent No.: US 9,101,757 B2
(45) Date of Patent: Aug. 11, 2015

(54) IMPLANTABLE LEAD HAVING AN ELONGATED LEAD BODY

(75) Inventors: Timo Frenzel, Berlin (DE); Michael Friedrich, Kleinmachnow (DE); Michelle Maxfield, Berlin (DE); Dagmar Buchner, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 325 days.

(21) Appl. No.: 13/282,685

(22) Filed: Oct. 27, 2011

(65) Prior Publication Data

US 2012/0103653 A1 May 3, 2012

Related U.S. Application Data

(60) Provisional application No. 61/407,474, filed on Oct. 28, 2010.

(51) Int. Cl.
*A61N 1/00* (2006.01)
*A61N 1/05* (2006.01)
*A61N 1/08* (2006.01)

(52) U.S. Cl.
CPC ......... *A61N 1/0563* (2013.01); *A61N 2001/086* (2013.01)

(58) Field of Classification Search
CPC ............. A61N 1/00; A61N 1/02; A61N 1/04; A61N 2/00; A61N 2/02; A61N 2/04
See application file for complete search history.

(56) References Cited

U.S. PATENT DOCUMENTS

2008/0051854 A1 2/2008 Bulkes et al.
2008/0243218 A1 10/2008 Bottomley et al.
2009/0099440 A1 4/2009 Viohl
2009/0270956 A1 10/2009 Vase et al.
2010/0256721 A1 10/2010 Weiss et al.

OTHER PUBLICATIONS

European Search Report and Notes to the European Search Report on European Patent Application No. EP 11 18 4588, dated Jan. 12, 2012 (7 pages).
Ladd, Mark E. and Quick, Harald H. (2000), "Reduction of Resonant RF Heating in Intravascular Catheters Using Coaxial Chokes", Magnetic Resonance in Medicine, Apr. 2000, vol. 43, pp. 615-619, Wiley-Liss, Inc.

*Primary Examiner* — Christopher D Koharski
*Assistant Examiner* — Elizabeth K So
(74) *Attorney, Agent, or Firm* — Buchanan Ingersoll & Rooney PC

(57) ABSTRACT

An implantable lead having an elongated lead body and a function conductor extending in the longitudinal direction of the conductor body, the function conductor being provided to implement a medical function of the lead, wherein in addition to the function conductor, a field decoupling conductor loop is provided, which reduces coupling of the function conductor to the outside alternating magnetic field by generating an induction field that is in the opposite direction of an outside magnetic field.

6 Claims, 4 Drawing Sheets

24b
30
23a
29
29a
23
25
21

IMPLANTABLE LEAD HAVING AN ELONGATED LEAD BODY

RELATED APPLICATION

This patent application claims the benefit of U.S. Provisional Patent Application No. 61/407,474, filed on Oct. 28, 2010, which is hereby incorporated by reference in its entirety.

TECHNICAL FIELD

The invention relates to implantable leads and, more particularly, an implantable lead having an elongated lead body and a function conductor extending in the longitudinal direction of the lead body, the conductor being provided to implement the medical function of the lead.

BACKGROUND

Such implantable leads are typically, in particular, stimulation electrode leads (at times also referred to in short as "electrodes") of cardiac pacemakers or shock electrode leads of implantable defibrillators, but they may also be catheters having an elongated conductive structure.

Medical implants, such as, for example, the pacemakers and defibrillators mentioned above, frequently have an electrical connection to the interior of the patient's body. Such a connection is used to measure electrical signals and/or to stimulate body cells. This connection is often configured as an oblong electrode. At present, electrical signals are transmitted between the implant and the electrode contacts (e.g., tip, rings, HV shock coils, sensors or the like) by way of materials offering good electrical conductivity.

When a system comprising an implant and an electrode is exposed to strong interference fields (e.g., EMI, MRI, etc.), undesirable error behavior may occur, especially the heating of parts of the system or electrical malfunctions (such as, for example, resets). Heating may result in damage to body tissue or organs when the heated parts have direct contact with the tissue. This is notably the case with the electrode tip.

The cause of the undesirable error behavior is the interaction of the field with the oblong lead structure of the electrode. The electrode acts as an antenna and receives energy from the surrounding fields. As the lead is used for treatment, the antenna can give off this energy distally by way of the electrode contacts (e.g., tip, ring, etc.) to the tissue, or proximally to the implant.

The same problems also occur with other oblong conductive structures, the proximal end of which is not necessarily connected to an implant (such as, for example, with catheters, temporary electrodes, and the like).

Shielded electrodes are known. In the prior art shielded electrodes, the shield of the electrode primarily acts against electrical fields that can be coupled from the outside. In addition, these shields are only effective and long-term stable when they have an appropriate shield strength. Consequently, a compromise must be found between enlarging the electrode diameter—with the attendant effects on costs and manageability of the electrode—and losses in the shielding effect.

In order to avoid interference due alternating magnetic fields, especially in magnetic resonance imaging (MRI) scanners, and more specifically to limit heating of the electrode tip in such fields, U.S. Publication No. 2008/0243218 proposes the provision of a protective conductor in an electrode lead which alternately turns back and forth in the longitudinal direction. This design, referred to as the billabong principle, also utilizes mutual inductances to reduce induced currents. However, in this case, an enlargement of the electrode diameter is also to be expected given the three-layer coil winding. In addition, the conductivity of the electrode will be lower.

From Ladd M., Quick H.: *Reduction of resonant RF heating in intravascular catheters using coaxial chokes*, Magnetic Resonance in Medicine, 2000, precautions are known against the heating, due to RF resonances, of intravascular catheters in the form of choke coils, referred to simply as chokes. Such chokes are located on the outer casing of the electrode and act against surface currents. However, this solution does not lower any currents that couple to the inside coil. In addition, an enlargement of the electrode diameter is to be expected, entailing the consequences described above.

The present invention is directed toward overcoming one or more of the above-mentioned problems It is an object of the invention to provide an improved implantable lead of the type mentioned above, which exhibits improved properties in strong outside alternating magnetic fields and which has a simple design and is therefore inexpensive to implement.

This object is achieved by an implantable lead having the characteristics of the independent claim(s). Advantageous refinements of the inventive concept are the subject matter of the dependent claims.

SUMMARY

An essential concept of the invention consists of reducing the influence of strong outside fields by providing a separate conductor loop in the implantable lead. The additional conductor loop, which in particular acts as a mutual inductance, changes the interaction between the outer field and the lead such that a different current distribution forms on the lead. The undesired antenna properties of the lead change as a result of this detuning. This leads to less heating of distal lead contacts. This advantage applies to different geometric shapes and different positions of the lead, as is understood by one skilled in the art.

In one embodiment of the invention, the proposed lead is configured as an electrode lead having an electrode connection at a proximal end and at least one stimulation, sensing and/or shock electrode at or close to a distal end, and a coiled function conductor extending between the electrode connection and the electrode. The conductor loop, acting as a field decoupling means, comprises a field decoupling coil that is wound in the insulated function conductor. This variant of the invention relates to extensively used stimulation and shock electrode leads of implantable pacemakers or cardioverters, and is therefore of particular practical relevance. Because the field decoupling coil is wound in the function conductor, an enlargement of the lead diameter, which occurs otherwise with shielded leads, is avoided.

In variants of this embodiment, it is provided that the electrode lead comprises a first and a second proximal electrode connection and a first and a second distal electrode, as well as a first function conductor extending between the first electrode connection and the first electrode and a second function conductor which extends between the second electrode connection and the second electrode. The second function conductor is wound in the same or opposite direction as the first function conductor. To this end, the conductor loop, acting as a field decoupling means, comprises at least one first functionally independent (high-resistance or high-impedance with respect to the function current) field decoupling coil which is wound in the first function conductor, and at least one second functionally independent (high-resistance or high-impedance with respect to the function current) field decoupling coil which is wound in the second function conductor and which proximally and distally is electrically connected in each case to the first field decoupling coil. This variant is also adapted to widely used products, and is therefore of particular practical value.

According to one design variant, the first field decoupling coil is proximally and distally electrically connected to the second field decoupling coil by an arbitrary electrical contact (for example, as a conductive ring acting as a sliding contact). Even more specifically, the conductive ring here can be embedded in insulation located between the first and second function conductors, and hence between the first field decoupling coil and the second field decoupling coil, and can be in sliding contact with the first and second field decoupling coils.

In a further design variant, at the proximal end of the lead, the electrical contact is positioned between the first and second field decoupling coils distally from the, or each, electrode connection and, at the distal end of the lead, the electrical contact is positioned between the first and second field decoupling coils proximally from the, or each, electrical contact between the, or each, function conductor and the, or each, electrode.

DESCRIPTION OF THE DRAWINGS

Advantages and functional characteristics of the invention will additionally become apparent hereinafter from the description of special and exemplary embodiments based on the figures. Shown are.

DETAILED DESCRIPTION

Figure 1A:
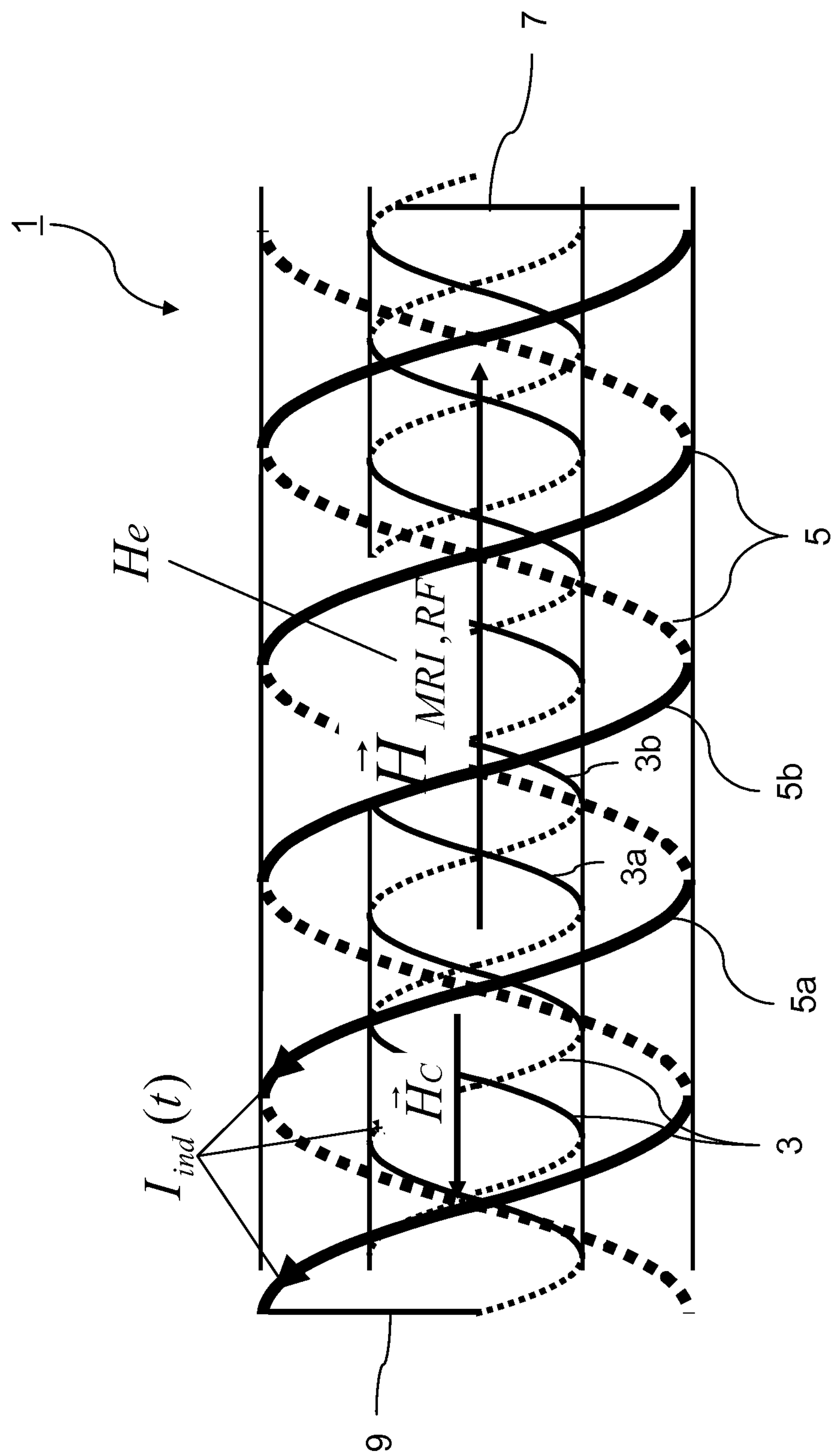
FIGS. 1A and 1B are schematic diagrams to explain the invention.

FIG. 1 is a schematic diagram to explain the invention, which shows, for clarity, only the conductive elements of an electrode lead 1 as an exemplary embodiment of an implantable lead, but not the insulating lead body thereof. In the embodiment shown, an inner conductor 3, which is formed by two wires wound inside each other, and an outer conductor 5, which likewise is formed by two wires wound inside each other, are provided. The inner 3 and outer 5 conductors are wound in opposite directions in this version. However, they can be wound in the same direction. During use, they can be exposed to an external alternating magnetic field $H_e$ which induces a current flow $I_{ind}(t)$ in the conductors 3 and 5.

The inner conductor (also referred to as "inner coil") 3 and the outer conductor (also referred to as "outer coil") 5 in each case comprise a function conductor 3*a* and 5*a*, which is used to implement a medical function of the electrode lead (for example, to transmit sensing signals or stimulation or shock pulses), and a field decoupling conductor 3*b* and 5*b*, which is functionally independent thereof and has no medical function and which, in particular, is not used for the signal or pulse transmission from or to the body tissue of a patient. The field decoupling conductors 3*b*, 5*b* are connected conductively to each other by a proximal contact 7 and a distal contact 9, whereby a closed conductor loop is formed between them, in which an induction current flows which generates a compensating field $H_c$ counteracting the outer field $H_e$.

Figure 1B:
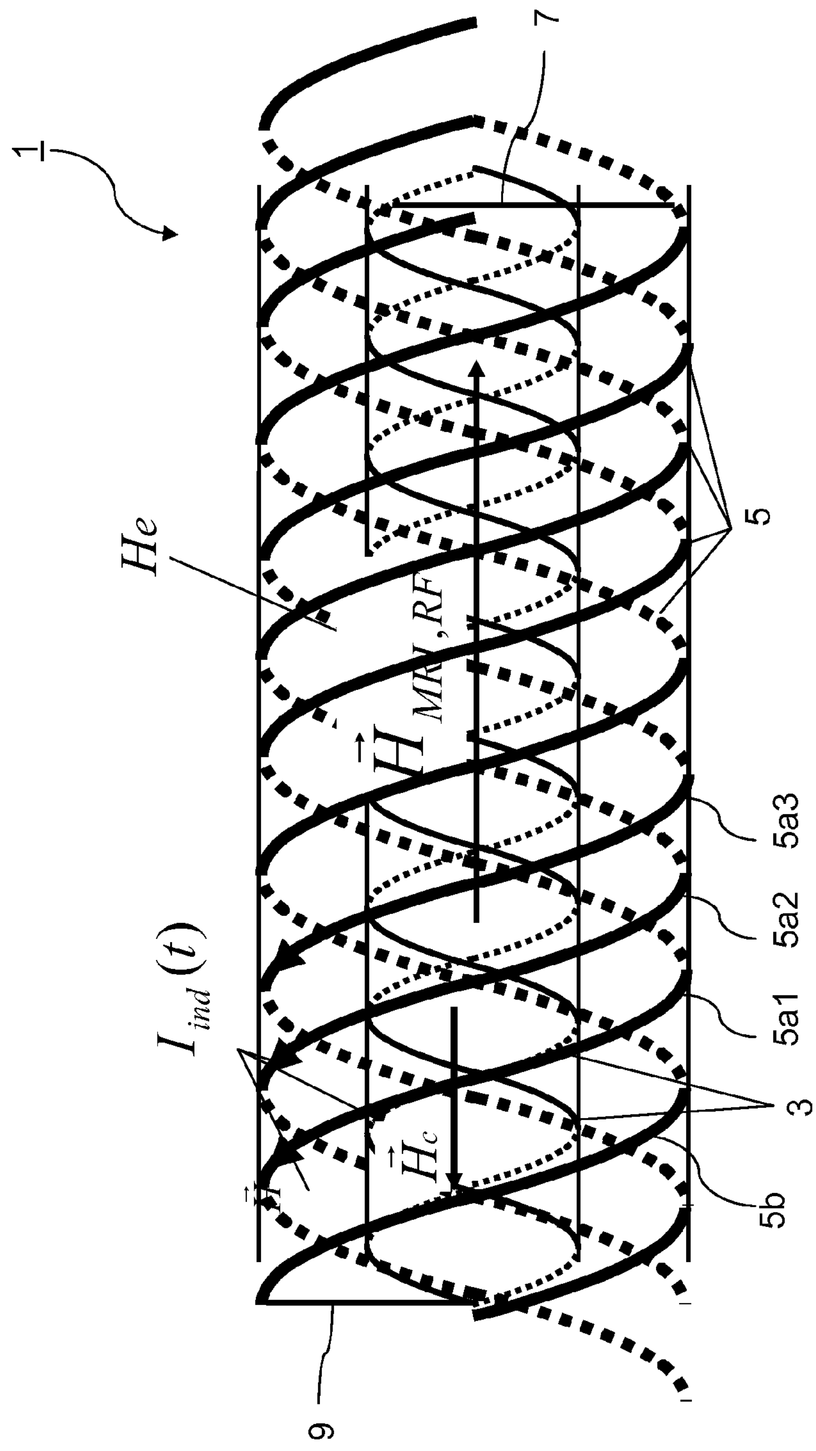

FIG. 1B shows a modified embodiment, wherein the same reference numbers are used to denote equivalent parts or parts exercising substantially similar effects as in the first embodiment shown in FIG. 1A, and these are not explained again. The essential difference, as compared to the first embodiment, is that the outer conductor (outer coil) 5 is quadruple coiled, which is to say four individual wires are wound inside each other, of which, the wires (individual coils) 5*a*1, 5*a*2 and 5*a*3 each perform a medical function, while the individual wire 5*b*, as in the first embodiment, is used together with the field decoupling conductor 3*b* of the inner coil 3 running in the opposite direction as an induction coil for (partial) field decoupling. This lead can be used to implement complex sensing, simulation and cardioversion functions, while at the same time offering protection against excessive heating of the electrodes coming in contact with the body tissue of the patient (electrode contacts).

Figure 2C:
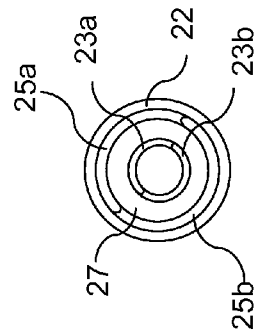
FIGS. 2A-2C are illustrations to explain one embodiment of the invention.
Figure 2A:
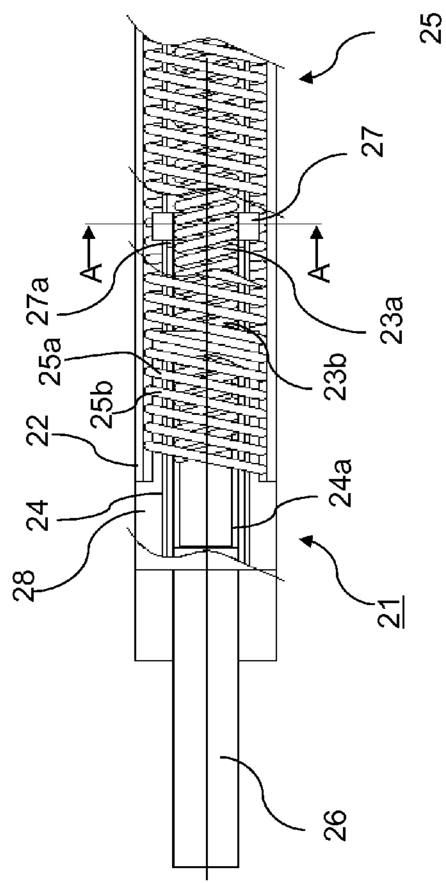
Figure 2B:
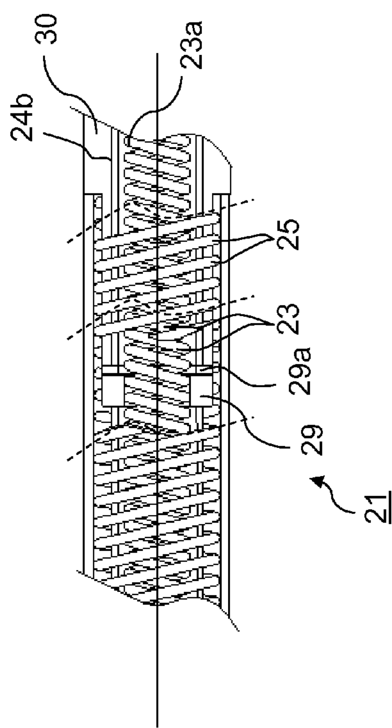

FIGS. 2A-2C show the example of a design variant of an electrode lead according to the invention, wherein FIG. 2A shows the proximal end section, FIG. 2B shows a distal section, and FIG. 2C shows a cross-section, and wherein elements that correspond to the schematic diagram of FIG. 1A are denoted with similar reference numbers as in that figure. The schematic illustration and subsequent explanations are not intended to provide a complete description of this electrode lead, but only special aspects of one embodiment of the invention.

The lead 21 comprises an insulating casing (also referred to as the lead body 22, made of silicone, for example), an at least double coiled inner conductor 23, an at least double coiled outer conductor 25 in this example, and an inner and a center insulating casing 24*a*, 24*b*. Electrode connection contacts 26, 28 are used to connect the respective function conductors 23*a*, 25*a* of the inner conductor 23 and the outer conductor 25 to an electronic medical device (not shown).

While the function conductors 23*a*, 25*a* are insulated over the longitudinal extensions thereof, non-insulated ("bare") wires are used herein as the field decoupling conductors 23*b*, 25*b*, and they are in electrical contact with each other in the proximal region of the electrode, and distally from the electrode connection contacts 26, 28, by way of a metal sleeve 27 in the manner of a sliding contact. The sliding contact makes it also possible to reliably maintain the electrical contact (and thereby keep the induction loop closed) even when the electrode lead is twisted and bent, without any significant mechanical stress—as it would inevitably be produced by fixed contact points—acting on the field decoupling conductors 23*b*, 25*b*. In the embodiment shown, a small insulating spacer sleeve 27*a* is provided as electrical insulation between the metal sleeve 27 and an electrode connection region of the inner conductor extending proximally there from.

FIG. 2B shows that the electrical contacting between the field decoupling conductors 23*b*, 25*b* of the inner coil 23 and outer coil 25 in the distal region of the electrode lead 21 is solved in the same manner as at the proximal end, which is by a (second) metal sleeve 29 acting as a sliding contact. Again, a (distally) neighboring spacer sleeve 29*a* ensures electrical insulation with respect to an annular electrode 30 of the electrode lead.

Figure 3:
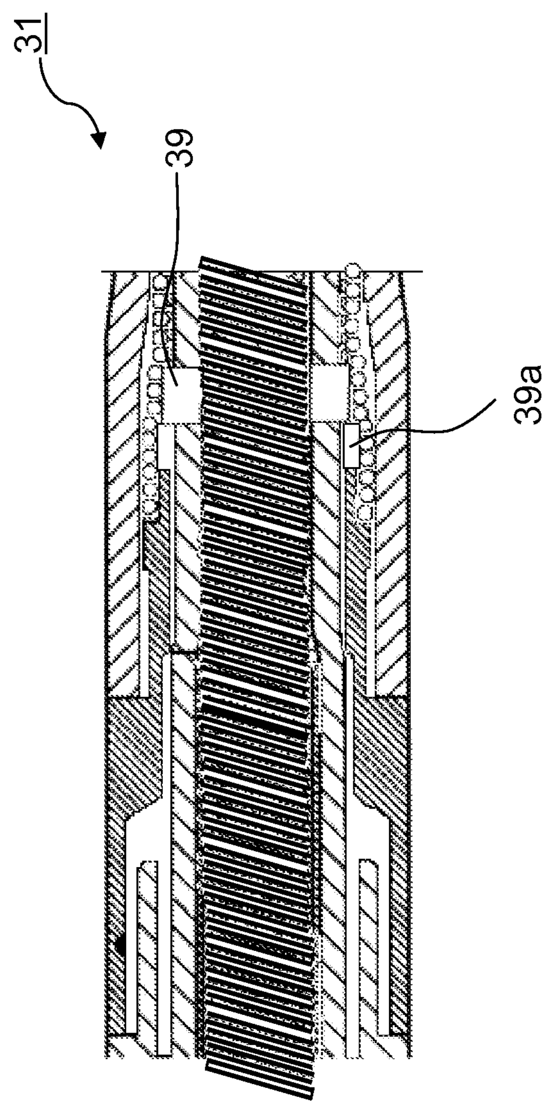
FIG. 3 is a detailed view of an electrode lead configured according to the invention.

FIG. 3 shows again the principle of the electrical contacting between the field decoupling conductors of the inner and outer coils by way of the metal sleeve (sliding contact) 39 with the associated insulating spacer sleeve 39*a*. For clarity, the remaining parts of the lead were not labeled here; in this respect, reference is made to the above explanations for FIGS. 2A-2C.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable lead comprising:

an elongated lead body having a proximal end and a distal end;

a first and a second proximal electrode connection at the proximal end;

a first and a second stimulating, sensing and/or shock electrode at or close to the distal end;

a first function conductor extending between the first proximal electrode connection and the first distal electrode;

a second function conductor extending between the second proximal electrode connection and the second distal electrode, wherein the second function conductor is wound in a same or opposite direction as the first function conductor, the second function conductor being provided to implement a medical function of the lead;

a field conducting conductor loop acting as a field decoupling means, the field conducting conductor loop comprising:

a first functionally independent field decoupling coil, which is wound in the first function conductor in an insulated manner; and a second functionally independent field decoupling coil, which is wound in the second function conductor in an insulated manner, wherein the second field decoupling coil is proximally and distally electrically connected to the first field decoupling coil at one or at several positions over the length of the electrode lead body by a conductive ring or coil section acting as a sliding contact;

wherein the conductive ring or the coil section is embedded in insulation located between the first and second function conductors and, hence, between the first field decoupling coil and the second field decoupling coil, wherein the conductive ring or the coil section is in sliding contact with the first and second field decoupling coils.

2. The implantable lead according to claim 1, wherein at the proximal end of the electrode lead the electrical contact is positioned between the first and second field decoupling coils distally from each electrode connection, and at the distal end of the electrode lead the electrical contact is positioned between the first and second field decoupling coils proximally from each electrical contact between each function conductor and each electrode.

3. An implantable lead comprising:

an elongated lead body;

an inner coil extending in a longitudinal direction of the elongated lead body, the inner coil comprising:

a first function conductor extending in a longitudinal direction of the elongated lead body, the first function conductor being provided to implement a medical function of the lead; and a first field decoupling conductor also extending in a longitudinal direction of the elongated lead body and independent of the first function conductor, the first field decoupling conductor having no medical function; and an outer coil extending in a longitudinal direction of the elongated lead body, the outer coil comprising:

a second function conductor extending in a longitudinal direction of the elongated lead body, the second function conductor being provided to implement a medical function of the lead; and a second field decoupling conductor also extending in a longitudinal direction of the elongated lead body and independent of the second function conductor, the second field decoupling conductor having no medical function;

wherein the first and second field decoupling conductors are connected together at proximal and distal ends of the lead to form a closed conductor loop which reduces coupling of the first and second function conductors to an outside alternating magnetic field by generating an induction field that is in an opposite direction of the outside alternating magnetic field, wherein the first field decoupling conductor is proximally and distally electrically connected to the second field decoupling conductor at one or at several positions over the length of the electrode lead body by a conductive ring or coil section acting as a sliding contact, and wherein the conductive ring or the coil section is embedded in insulation located between the first and second function conductors and, hence, between the first field decoupling conductor and the second field decoupling conductor, wherein the conductive ring or the coil section is in sliding contact with the first and second field decoupling conductors.

4. The implantable lead according to claim 3, wherein the inner coil is wound in a same or opposite direction as the outer coil.

5. The implantable lead according to claim 3, wherein the outer coil is quadruple coiled having three wires forming the second function conductor and being provided to implement a medical function of the lead and one wire forming the second field decoupling conductor and having no medical function.

6. The implantable lead according to claim 3, wherein at the proximal end of the electrode lead the electrical contact is positioned between the first and second field decoupling conductors distally from each electrode connection, and at the distal end of the electrode lead the electrical contact is positioned between the first and second field decoupling conductors proximally from each electrical contact between each function conductor and each electrode.

* * * * *